(12) United States Patent
Britton et al.

(10) Patent No.: US 6,343,690 B1
(45) Date of Patent: Feb. 5, 2002

(54) SPECIMEN CARRIER FOR AUTOMATED TRANSPORT SYSTEM AND METHOD AND APPARATUS FOR IDENTIFYING SAME

(75) Inventors: Ted W. Britton, Sunrise; Valentin Quesada, Hialeah; Craig Veiner, Miami, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/420,307

(22) Filed: Oct. 18, 1999

(51) Int. Cl.⁷ .............................................. B65G 29/00
(52) U.S. Cl. ................... 198/867.06; 198/803.6
(58) Field of Search .................. 198/465.1, 867.11, 198/867.06, 803.8, 349, 360, 803.7, 867.13

(56) References Cited

U.S. PATENT DOCUMENTS

| | | | |
|---|---|---|---|
| 5,478,184 A | * 12/1995 | Bryant et al. | ............. 198/347.1 |
| 5,623,415 A | 4/1997 | O'Bryan et al. | |
| 5,676,514 A | * 10/1997 | Higman et al. | ........ 198/370.01 |
| 5,941,366 A | 8/1999 | Quinlan et al. | |
| 6,157,300 A | * 12/2000 | Quaderer et al. | ........... 198/341 |

FOREIGN PATENT DOCUMENTS

CA 2216052 9/1997

* cited by examiner

Primary Examiner—Kenneth W. Noland
(74) Attorney, Agent, or Firm—Warren W. Kurz; Mitchell E. Alter

(57) ABSTRACT

A specimen carrier comprises a unitary structure for receiving and retaining a specimen container in an upright orientation. Such unitary structure is defined by a pedestal having upper and lower platforms connected by a stem. Extending upwardly from the upper platform is a plurality of rigid members which support a plurality of opposing flexible fingers adapted to engage and press upon the side wall of a specimen container received by the carrier. Preferably, the specimen carrier of the invention has a chamber formed therein for housing a pre-programmed, programmable or otherwise radio-frequency (RF) identification tag in the form of an RF transponder. Upon being energized by a suitable RF field provided by an RF reader antenna or sensor positioned adjacent the carrier's intended path of movement, the tag transmits a unique identification code, such code being received by the antenna or sensor and decoded by the reader.

9 Claims, 3 Drawing Sheets

SPECIMEN CARRIER FOR AUTOMATED TRANSPORT SYSTEM AND METHOD AND APPARATUS FOR IDENTIFYING SAME

BACKGROUND OF THE INVENTION

1. Field of the Invention

The present invention relates to automated conveying systems for transporting biological and chemical specimens and the like, e.g., vials of blood, along a predetermined transport path, e.g., from a loading station to a work station for analysis or processing. More particularly, this invention relates to improvements in specimen carriers adapted to be transported by a conveyor system while supporting a specimen container in a generally upright orientation, and to methods and apparatus for identifying such carriers as they are transported. Another aspect of this invention relates to methods and apparatus for identifying such carriers.

2. Discussion of the Prior Art

Automated systems for analyzing various properties of biological and chemical specimens are well known. In certain automated blood analyzing systems, for example, a conveyor belt or the like serves to transport individual containers (e.g., vials or test tubes) of blood along a predetermined path, and blood analyzing or processing instruments positioned along such path operate to extract and process a blood sample from each container as and when presented to it. Such instruments may include, for example, one or more hematology instruments for performing red and white cell analyses on the sample, flow cytometers for identifying cell types through fluorescence measurements, coagulation instruments for measuring a blood sample's coagulation time, and slide-making instruments for making blood smears on microscope slides for subsequent analysis. Such instruments often comprise a dedicated aspiration mechanism including an aspiration needle or probe which serves to puncture a seal on the specimen container and to aspirate a portion of the sample within. Typically, the aspiration needle is designed to move vertically as it enters and exits the specimen container. Thus, to facilitate sample aspiration, as well as to avoid any spillage of the sample during transport through the system, it is usually desirable to support the container in a vertically upright orientation at all times. Further, to properly correlate the test results with the different blood samples tested, as well as to be able to selectively route the specimen containers through the instrument system so that only those processes requested are actually performed on a given sample, it is desirable to provide some means for identifying each sample container as it moves through the automated system.

To maintain specimen containers of various sizes in an upright orientation while transiting an automated instrument system, it is common to support each container in a specimen carrier, sometimes referred to as a "puck." The specimen carrier, which is adapted to receive and retain containers of different diameters and lengths, is designed to interact with the elements of the conveyor system in assuring that each specimen container supported by the carrier is properly routed. To keep track of each of many biological specimen containers transported by an automated system of the above type, it is common to affix a barcode label to each container and to position barcode readers at strategic fixed locations along the conveyor path to read such labels. Each barcode label provides, for example, encoded patient identification data, test types to be performed, and all other information required to assure that the specimen is properly processed and routed through the automated system. The respective outputs of the barcode readers are suitably processed by a computer-based laboratory information system to relate the information on the labels with the processing to be performed. Automated blood analyzing systems of this type are disclosed, for example, in U.S. Pat. No. 5,623,415 and in the published Canadian Patent Application No. 2,216,052, laid open on Mar. 19, 1998.

In the above-noted Canadian Patent Application, an automated transport system is disclosed for transporting biospecimens (e.g., blood and urine) to different test sites. In this system, each biospecimen container (a test tube or vial) is received and transported in a carrier that functions to assure that its respective container is supported in an upright or vertical orientation so that its mouth can be centered relative to an aspiration probe or needle used to extract sample from the container. Each carrier comprises a cylindrically shaped base from which at least three container-retaining members extend upwardly. The retaining members, which are preferably made of heavy gauge stainless steel wire, are equally spaced about the perimeter of the base, and together they define, with the top of the base, a container reception site. Preferably, each of the retainer members is relatively narrow or slender in shape (compared to the surface area of the retained container) so as not to obscure a major portion of a barcode label carried by a container. One end of each retainer member is mechanically latched to the base member by inserting it into a notch in the base and rotating it to position an intermediate portion into an arcuate groove. The respective opposite ends (i.e., the free ends) of the retainer members are biased towards the central axis of the container-reception site so that, collectively, they can receive and retain specimen containers of different diameters. In the preferred embodiment, an O-ring surrounding the free ends of the three retainer members is used to provide the biasing feature. Also disclosed in this application is the use of a programmable magnetic identification system, including a magnetic identification device embedded in the carrier base and read by an appropriate reader to uniquely identify a specimen carrier. This carrier identification scheme is used in conjunction with, or instead of, the indicia carried by the specimen container.

While container carriers of the type disclosed in the above Canadian application might prove useful in transporting specimen containers in an automated transport system, these containers are disadvantageous from the standpoints of manufacturing cost and complexity. For example, the procedure for connecting the retainer members to the base member is labor-intensive and ideally should be avoided. Further, the suggested magnetic identification system, while plausible, is disadvantageous in that it can be readily corrupted, and even erased, by any significant field-generating stimuli in or near the conveyor system; thus, care must be exercised in the system design to provide proper shielding to prevent any magnetic structure in the area from interfering with the magnetic circuit between the carrier's embedded magnetic tag and the magnetic reader. Further, in a magnetic system, it is difficult to control the extent of the reader's magnetic interrogation field, thereby making it difficult to unambiguously differentiate adjacent carriers on the conveyor.

Recently, radio-frequency (RF) identification tags in the form of small disks have been used for identification and tracking purposes. Such tags have been used primarily for identifying and tracking animals in which they have been implanted. Each tag is pre-programmed with a unique identification code and/or other information of specific interest that can be read-out as the animal enters an RF field produced by the loop antenna of an RF transceiver or reader. The energy from the transceiver acts to energize the RF tag, thereby enabling the tag to transmit its identification code and any other information of interest, including information that has been written to the tag while in use. The transceiver is adapted to read the identification code over a relatively large range and provide an appropriate output signal. Such RF identification systems are commercially available, e.g., from Intersoft, Estill Springs, Tenn. Owing to the relatively large interrogation fields associated with such systems, they would be impractical for use in a miniaturized specimen conveyor system of the type described above. More particularly, the RF interrogation field is so extensive that it would simultaneously energize multiple tags, making it difficult to selectively detect a single specimen among many other closely spaced specimens. Moreover, due to the large loop area of the antennas used in such RF systems, large electromagnetic and electrostatic fields are produced which may affect devices outside the localized environments. These large antennas are also susceptible to external noise typically present in the medical environment.

SUMMARY OF THE INVENTION

In view of the foregoing discussion, an object of this invention is to provide an improved container carrier of the above type, a container carrier that is improved from the standpoint that it is less labor-intensive and costly to fabricate.

Another object of this invention is to provide an improved container carrier of the above type, one that carries an identification tag that is not as corruptible as the magnetic identification scheme proposed by the aforementioned prior art.

Yet another object of this invention is to provide an improved method and apparatus for identifying objects, such as the specimen carriers of the invention, moving together on a conveyor.

According to a preferred embodiment of the invention, a specimen carrier comprises a unitary structure for receiving and retaining a specimen container in an upright orientation. Such unitary structure is defined by a pedestal having upper and lower platforms connected by a stem. Extending upwardly from the upper platform is a plurality of rigid members equally spaced from a central axis passing through the platforms. Extending angularly downward from a free end of each rigid member, toward such central axis, is a flexible finger adapted to engage and press upon the side wall of a container received by the carrier. Collectively, the flexible fingers carried by the rigid members define a container site for receiving and retaining specimen containers of different diameters. Preferably, the unitary structure is made of a moldable thermoplastic chosen for its flexural properties.

According to another aspect of the invention, the specimen carrier of the invention has a chamber formed therein that houses a programmable radio-frequency (RF) identification tag in the form of an RF transponder. Upon being energized by a suitable RF field provided by a specialized RF antenna positioned adjacent the carrier's intended path of movement, the tag transmits a unique identification code, such code being received by such antenna and decoded by its associated RF reader.

According to another aspect of this invention, a new and improved method for identifying objects moving in an automated conveyor system is provided. Such method comprises the steps of coupling a programmable radio-frequency (RF) identification tag in the form of an RF transponder to the object, such RF transponder being selectively energizable by RF electromagnetic energy to transmit a unique identification code that differentiates that object from other objects; and transmitting RF electromagnetic energy from a location proximate the path and at an energy level adapted to selectively energize only one identification tag coupled to an object moving along the path.

As a result of the invention, the manufacturing costs of container-carriers of the type described are significantly reduced, and an unambiguous identification of the carrier, or any other information carried by the carrier's RF tag is provided.

The invention and its advantages will be better understood from the ensuing detailed description of a preferred embodiment, reference being made to the accompanying drawings.

DETAILED DESCRIPTION OF A PREFERRED EMBODIMENT

Figure 1:
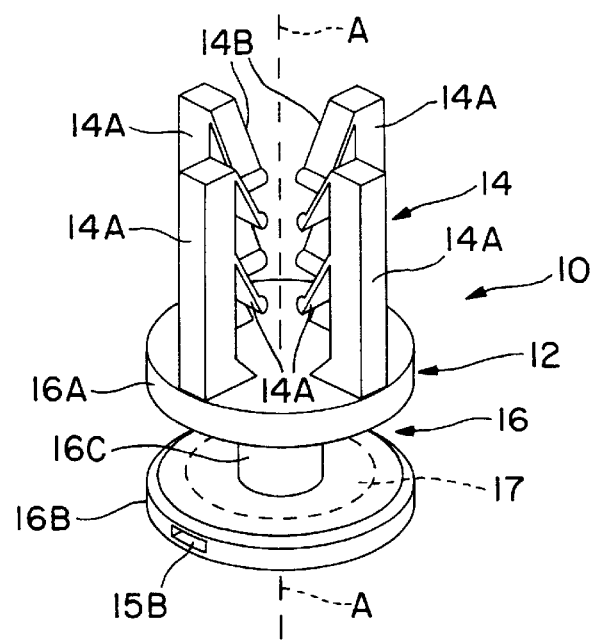
FIG. 1 is a perspective view of a container carrier of the present invention.
Figure 4:
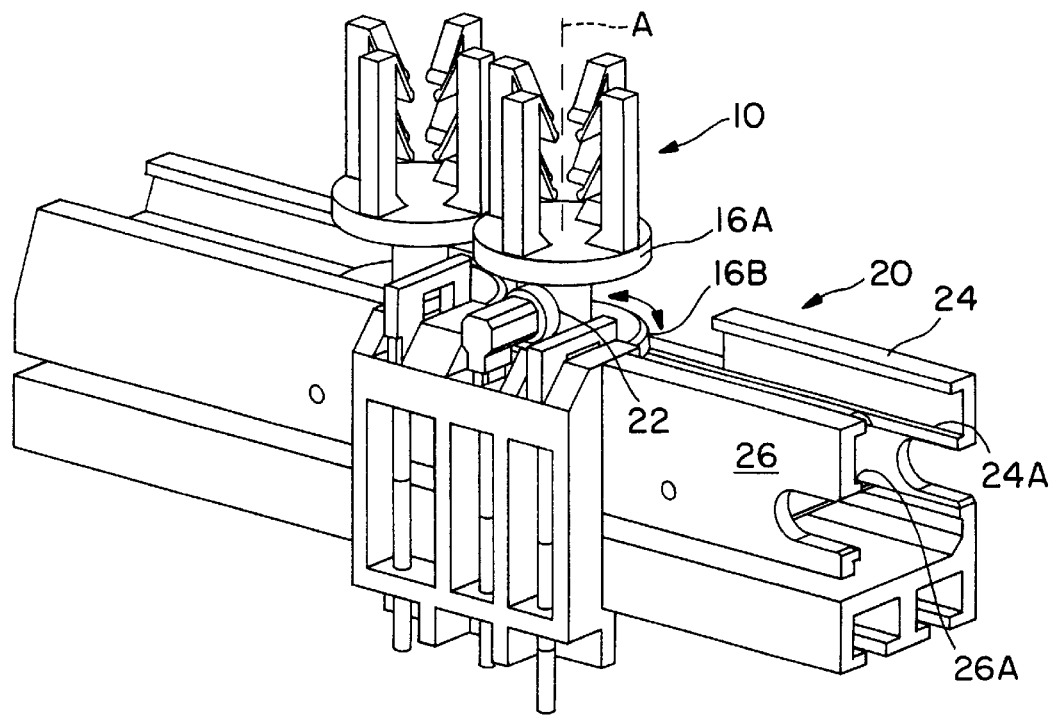
FIG. 4 is a perspective illustration of a portion of a conveyor system for transporting and turning the FIG. 1 device.
Figure 2:
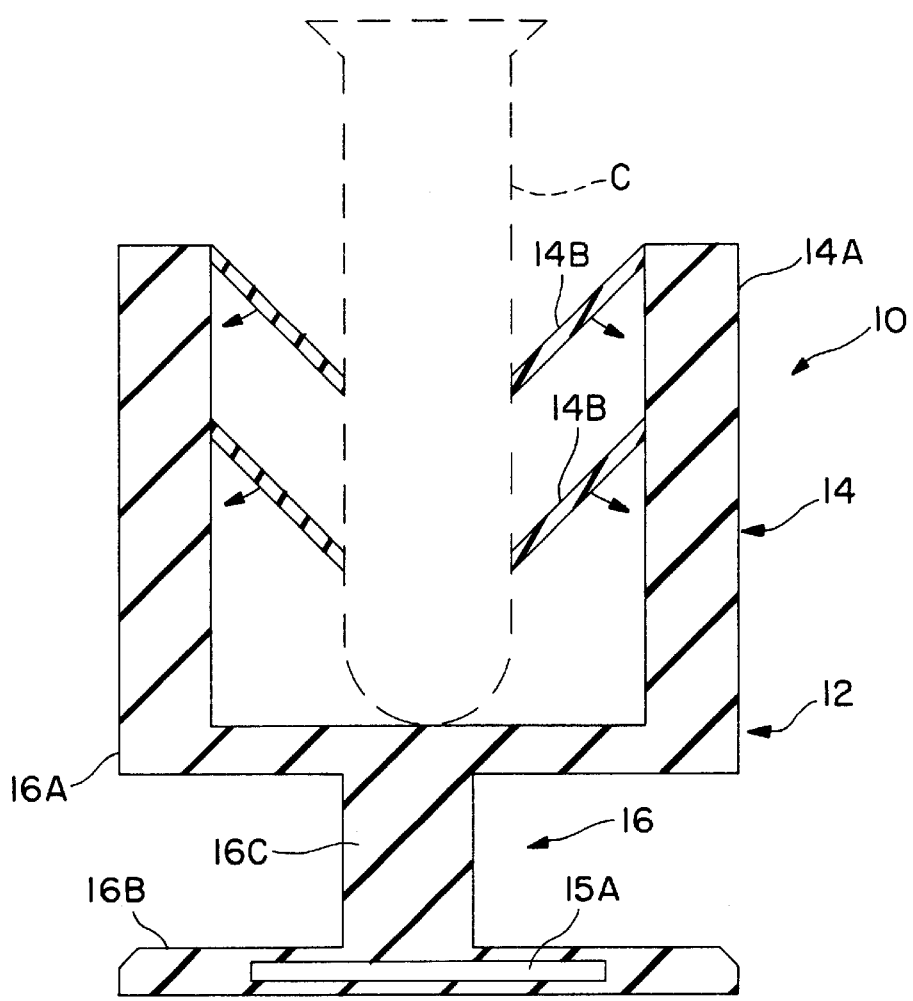
FIG. 2 is a cross-sectional illustration of the FIG. 1 device.

Referring now to the drawings, FIG. 1 illustrates a specimen carrier 10 adapted to be transported by an automated conveyor system while supporting a cylindrically-shaped specimen container, e.g. a test tube or vial, in a generally upright orientation. A portion of such conveyor system is shown in FIG. 4. Carrier 10 preferably comprises a unitary (i.e., one-piece) structure 12 defining (i) a container-retaining portion 14 for receiving, supporting and retaining a specimen container C (shown in FIG. 2) in an upright orientation; and (ii) a pedestal portion 16 adapted to be engaged and manipulated by certain components of the automated conveyor system for the purpose of advancing the carrier along a predetermined path and for selectively rotating the carrier about a central axis A so that, for example, a barcode label on the container or carrier can be more easily read by a barcode reader positioned along the transport path. The container-retaining portion 14 comprises a plurality of rigid members 14A, preferably four in number, that are equally spaced from and extend generally parallel to the central axis A. Each rigid member extends perpendicularly upward from the pedestal portion 16, and each has one or more flexible fingers 14B extending angularly downward from its distal end portion, toward the central axis A. Each of the flexible fingers is adapted to be flexed away from axis A as a container is inserted, and to engage and press upon the sidewall of a specimen container C received by the carrier. Thus, owing to the flexible nature of the fingers 14B, containers of different sizes can be received and retained by the container-retaining portion 14 with the carrier's central axis substantially coinciding with that of the carrier, as is important to reliable cap-piercing, aspiration and indexing.

The pedestal portion 16 of the carrier comprises a pair of platforms 16A and 16B spaced by an interconnecting stem 16C. The upper platform 16A supports the aforementioned rigid members 14A of the container-retaining portion 14, and the lower platform 16B contains a chamber 17 for housing a radio-frequency (RF) identification tag, as described below. The spacing between the platforms is such as to enable a idler pinch roller 22, shown in FIG. 4 and forming part of the automated conveying system 20, to frictionally engage and act upon the top surface of lower platform 16B to impart a rotational movement of the carrier about axis A so that a barcode reader (not shown) can read a barcode carried by either the carrier or, more preferably, the outer surface of a specimen container C supported by the carrier. Preferably, the platform members of the pedestal portion are circular in shape, each having the same diameter of about 30 mm. The diameter of platform 16A is selected to fit between the opposing rails 24,26 of the conveyor system 20 and be supported by the conveyor belt portion. The chamber 15 formed within platform 16A is approximately 2 mm in height and 22 mm in diameter. A pair of opposing access openings 15A and 15B are provided for inserting an RF identification tag and, if necessary, for ejecting such tag once positioned within the chamber.

As noted above, the carrier is a unitary structure, preferably being molded from a suitable plastic chosen for its low friction and high flexural properties. A preferred plastic is Noryl® N225, a modified polyphenyloxide manufactured by G.E. Plastics. Preferably, the carrier is injection-molded in two pieces, symmetrical with respect to axis A, that are subsequently bonded together to encapsulate the RF tag. Alternatively, the RF tag can be inserted into chamber 15 after such bonding through opening 15A.

Figure 3A:
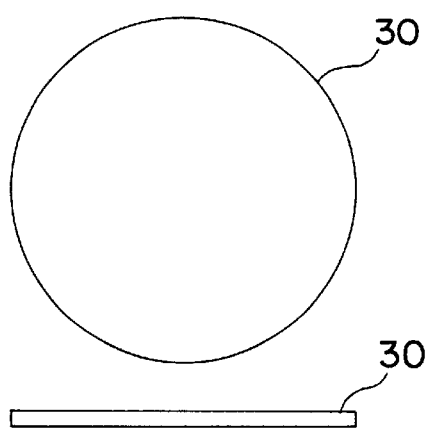
FIGS. 3A and 3B are schematic illustrations of an RF identification system.
Figure 3B:
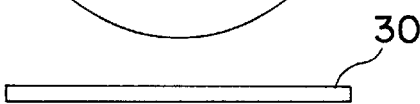
Figure 5:
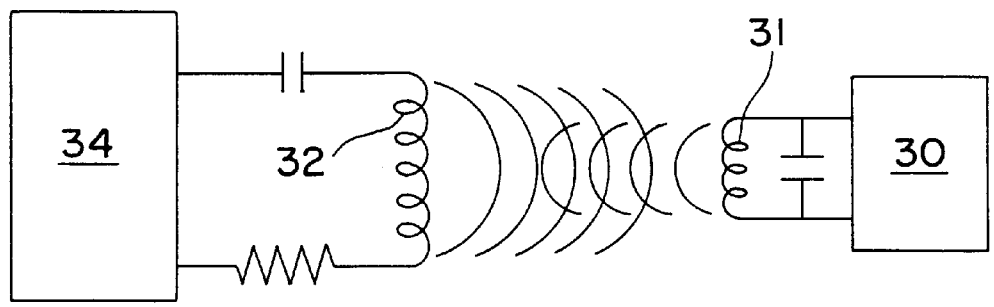
FIG. 5 is a schematic illustration of an RF identification system.
Figure 6A:
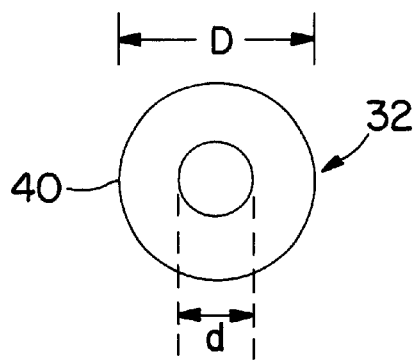
FIGS. 6A and 6B illustrate a preferred RF antenna design.
Figure 6B:
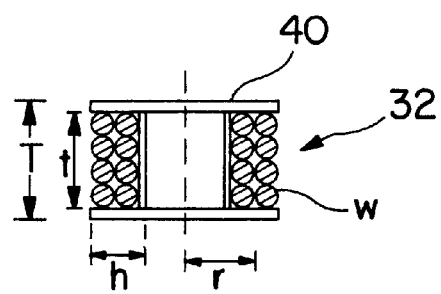

A preferred RF identification tag 30 is shown in FIGS. 3A and 3B. Tag 30 has a disk-like shape with a thickness of about 1 mm and a diameter of about 20 mm. Tag 30 is actually a small, yet sophisticated radio transceiver that is normally passive in nature. It contains a tuned antenna-capacitor circuit and a microchip that is preprogrammed to transmit an AM (amplitude-modulated) data stream through its antenna 31 (shown in FIG. 5) representing a unique identification code. The tag is "powered-up" and thereby becomes active only when subjected to an RF field generated by a tuned antenna 32 of an RF reader circuit 34. Preferably, the antenna 32 of the RF reader is of a size suitable for positioning in the bed of conveyor system at strategic locations along the conveyor path. The field produced by the RF reader must be sufficiently restricted as to activate only the RF tag of the closest carrier and no other, or to selectively receive only the signal from the closest carrier. Upon being activated, the RF tag begins to transmit its unique identification code. In addition to energizing the RF tag, the reader operates to demodulate and decode the tag's AM transmission. The output of the reader (provided on a serial port) is used to control the processing of the container whose tag is read. RF identification tags have been used heretofore for animal identification, access and inventory control, race timing and various other purposes; to date, however, they have not been used to identify objects moving side-by-side and virtually contiguous, as is common in an automated conveyor system. As noted above, RF tags and readers are generally available from Intersoft, Estill Springs, Tenn., and the RF tag of the preferred embodiment of this invention is Intersoft's Model EDP20RO. While this RF tag can be used as provided by Intersoft, the corresponding reader (made by Intersoft) cannot be used owing to its loop antenna design, which provides a relatively long-range tag-activating RF field. In the present embodiment, a relatively small bobbin-type antenna replaces such loop antenna. Such an antenna is illustrated in the top plan and sectional views of FIGS. 6A and 6B, respectively. The outer diameter D and thickness T of the bobbin 40 is selected to fit within the bed of the conveyor track, directly beneath the carrier transport path. The bobbin's inner diameter d and thickness D, and the number of turns and gauge of the wire W wrapped about the bobbin is selected to produce a tag-energizing RF field only in the immediate vicinity of the bobbin so that the RF tag of only a single carrier is energized as it passes directly above the antenna at the nominal transport speed. The tag detection and segregation is optimal when the antenna field is parallel to the equatorial axis of the tag's antenna 31. It will be appreciated that the antenna field characteristics can be controlled in a variety of methods applicable to the antenna circuit. A particularly preferred bobbin antenna design comprises a length of 38 gauge wire (0.0039 inches in diameter) wound about a bobbin to provide a coil having an average radius of 0.3 inches and a height h of 0.29 inches and a thickness t of 0.069 inches.

The invention has been described with reference to a preferred embodiment. It will be appreciated, however, that obvious variations can be made without departing from the spirit of the invention, and such variations are intended to fall within the scope of the appended claims.

What is claimed is:

1. A specimen carrier adapted to be transported by an automated conveyor system while supporting a specimen container in a generally upright orientation, said specimen carrier comprising:

a unitary structure defining (i) a pedestal portion adapted to be engaged and manipulated by components of said automated conveyor system for the purpose of advancing the carrier along a desired path and for selectively rotating the carrier about a vertical axis, said pedestal portion comprising spaced apart upper and lower platforms interconnected by a stem; and (ii) a container-retaining portion for receiving, supporting and retaining a specimen container in a desired orientation, said container-retaining portion comprising (a) a plurality of rigid members equally spaced from a central axis passing through the platforms and extending upwardly from the upper platform, and (b) a plurality of flexible fingers, one or more of said fingers extending angularly downward from a distal end portion of each rigid member, towards said central axis, each of said flexible fingers being adapted to engage and press upon the side wall of a container received by the carrier, said flexible fingers collectively defining a container site for receiving, centering and retaining specimen containers.

2. The specimen container carrier defined by claim 1 wherein said unitary structure further defines a chamber for housing a programmable radio-frequency (RF) identification tag in the form of an RF transponder.

3. The specimen container carrier defined by claim 2 wherein said chamber is formed in said pedestal portion.

4. The specimen container carrier defined by claim 1 wherein said chamber is formed in the lower platform of said pedestal portion.

5. The specimen container carrier defined by claim 1 wherein said unitary structure further defines a chamber in said lower platform of said pedestal portion, and wherein a radio-frequency (RF) identification tag in the form of an RF transponder is disposed in said chamber.

6. The specimen container carrier defined by claim 1 wherein said unitary structure is formed of an injection-moldable plastic.

7. The specimen container carrier defined by claim 1 wherein said container-retaining portion comprises four of said rigid members, and wherein each of said rigid members supports at least two of said fingers.

8. A specimen carrier adapted to be transported by an automated conveyor system while supporting a specimen container for processing, said specimen carrier comprising:

a unitary structure defining (i) a pedestal portion adapted to be engaged an manipulated by components of said automated conveyor system for the purpose of advancing the carrier along a desired path; and (ii) a container-retaining portion for receiving, supporting and retaining a specimen container in a desired orientation, said unitary structure defining a chamber containing a programmable radio-frequency (RF) identification tag in the form of an RF transponder that is selectively energizable by RF electromagnetic energy.

9. An identification system for identifying specimen carriers moving along a desired path, each of said specimen carriers comprising a unitary structure defining a pedestal portion adapted to be engaged and manipulated by components of said automated conveyor system for the purpose of advancing the specimen carrier along said desired path, and a container-retaining portion for receiving, supporting and retaining a specimen container in a desired orientation, said unitary structure further defining a chamber therein; said identification system comprising:

(a) a radio-frequency (RF) transponder disposed in each of the respective chambers of said specimen carriers, said RF transponder being selectively energizable by RF electromagnetic energy to transmit a unique identification code that differentiates each specimen carrier from all others; and (b) a transceiver including a bobbin antenna for transmitting electromagnetic energy from a location immediately adjacent said desired path at an energy level and at a frequency adapted to selectively energize only one the RF transponders associated with a specimen carrier moving along said desired path.

* * * * *